United States Patent [19]

Tadanier et al.

[11] 4,252,972
[45] Feb. 24, 1981

[54] FORTIMICIN B-1,2:4,5-BIS-CARBAMATES

[75] Inventors: John S. Tadanier; Jerry R. Martin, both of Waukegan, Ill.

[73] Assignee: Abbott Laboratories, North Chicago, Ill.

[21] Appl. No.: 79,136

[22] Filed: Sep. 26, 1979

[51] Int. Cl.$^3$ ............................................. G07H 15/22
[52] U.S. Cl. .................................. 536/17 R; 548/218; 424/180
[58] Field of Search ...................... 548/218; 536/17 R; 424/180

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,091,032 | 5/1978 | Tadanier et al. | 424/118 |
| 4,124,756 | 11/1978 | Martin et al. | 536/17 R |
| 4,169,198 | 9/1979 | Martin et al. | 536/17 R |
| 4,169,942 | 10/1979 | Mochida et al. | 424/180 |
| 4,176,178 | 11/1979 | Martin et al. | 536/17 R |
| 4,183,290 | 1/1980 | Kurath et al. | 536/17 R |
| 4,187,296 | 2/1980 | Tadanier et al. | 536/17 R |
| 4,187,297 | 2/1980 | Martin et al. | 536/17 R |
| 4,187,298 | 2/1980 | Martin | 536/17 R |
| 4,187,920 | 2/1980 | Post | 536/17 R |
| 4,192,867 | 3/1980 | Martin et al. | 536/17 R |

OTHER PUBLICATIONS

Rodriguez et al., Carbohydrate Research, vol. 59, pp. 240–243 (1977).

Umezawa et al., Bull. Chem. Soc. Japan; vol. 44, pp. 1411–1415 (1971).

*Primary Examiner*—Mary C. Lee
*Attorney, Agent, or Firm*—Robert L. Niblack; Gildo E. Fato; Joyce R. Niblack

[57] ABSTRACT

2′,6′-Di-N-benzyloxycarbonylfortimicin B-1,2:4,5-bis-carbamate and fortimicin B-1,2:4,5-bis-carbamate and its salt are provided by the present invention. The compound is represented by the formula

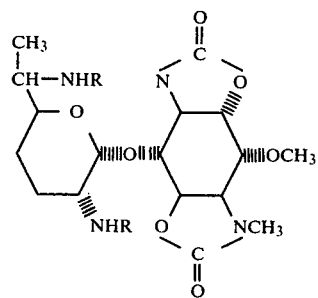

wherein each R is either hydrogen or benzyloxycarbonyl The bis-carbamate is useful as in intermediate in the preparation of fortamine bis-carbamate, which in turn is useful as an intermediate in the preparation of aminoglycoside antibiotics via glycosidation with suitably protected sugar moieties.

2 Claims, No Drawings

FORTIMICIN B-1,2:4,5-BIS-CARBAMATES

BACKGROUND OF THE INVENTION

The aminoglycoside antibiotics are a well recognized, useful class of antibiotics. One of the most recently recognized aminoglycoside antibiotic families has been the fortimicin family of antibiotics. See U.S. Pat. Nos. 3,976,768 and 3,931,400 which disclose fortimicins A and B.

As with other antibiotics, chemical modification of the fortimicin family of antibiotics has provided useful entities which are either intrinsically more active than the parent antibiotics, have activity against resistant strains of organisms or have reduced toxicity.

Heretofore, it has been necessary to produce fortimicin B and chemically modify that parent antibiotic in order to obtain the desired derivative and this has often required reaction involving numerous, complicated steps.

It has now been found that by converting a suitably protected fortimicin B to the bis-carbamate, and cleaving the glycoside bond to obtain fortamine-bis-carbamate, a number of aminoglycoside antibiotics can be readily prepared simply by reacting the protected fortamine with a suitably protected sugar, in the case of the fortimicins, with a suitably protected purpurosamine as taught in commonly assigned, co-pending U.S. Ser. No. 079,131 filed of even date with the present application.

SUMMARY OF THE DISCLOSURE

2'6'-Di-N-benzyloxycarbonylfortimicin B-1,2:4,5-bis-carbamate and its preparation is disclosed herein.

DETAILED DESCRIPTION OF PREFERRED EMBODIMENTS

The present invention provides the compound 2'6'-di-N-benzyloxycarbonylfortimicin B-1,2:4,5-bis-carbamate. The compound is represented by the formula:

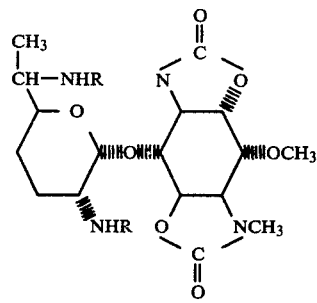

wherein R is benzyloxycarbonyl or hydrogen.

The compounds of this invention are useful in the preparation of fortamine-1,2:4,5-bis-carbamate which is useful in the direct synthesis of aminoglycoside antibiotics by glycosidation with a suitably protected sugar moiety such as a purpurosamine as taught in commonly assigned, co-pending application U.S. Ser. No. 079,131 filed of even date herewith.

The preparation of the compound of this invention is summarized in the following reaction scheme and described in detail in the following examples.

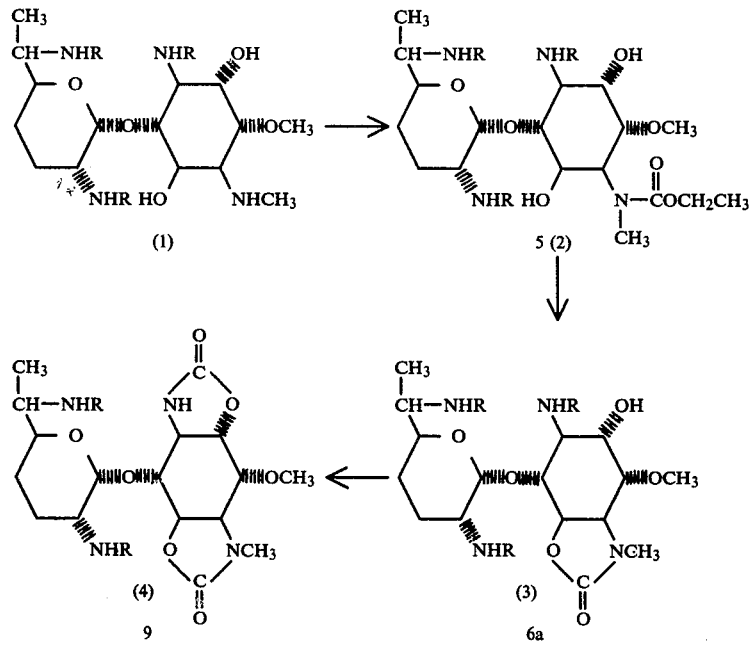

The following examples further illustrate the present invention.

EXAMPLE 1

1,2',6'-Tri-N-benzyloxycarbonylfortimicin B(1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide [234:1.4:0.1(v/v/v)] gives 1.05 g of product (1):$[\alpha]_D^{25}$ −16.5° (c 1.0,CH$_3$OH); IR(CDCl$_3$) 1712 and 1507 cm$^{-1}$.

EXAMPLE 2

4-N-Ethoxycarbonyl-1,2′,6′-tri-N-benzyloxycarbonylfortimicin B(2)

To a magnetically stirred solution of 3.02 g of 1,2′,6′-tri-N-benzyloxycarbonylfortimicin B(1), 130 ml of methanol and 60 ml of a solution of 3.02 g of sodium bicarbonate in 72 ml of water is added 0.90 ml of ethyl chloroformate. Stirring is continued at room temperature for 3 hours. The major portion of the methanol is evaporated under reduced pressure and the residue is shaken with a mixture of 200 ml of chloroform and 200 ml of 5% aqueous sodium bicarbonate. The chloroform solution is separated and washed with 200 ml of water. The aqueous solutions are washed in series with four 100 ml portions of chloroform. The chloroform solutions are combined, and the chloroform is evaporated under reduced pressure leaving 3.36 g of white glass. The latter is chromatographed on 250 g of silica gel packed and eluted with benzene-methanol [95;15(v/v)] to yield 2.57 g of the desired product (2).NMR(CDCl$_3$)$\delta$ 1.15d(J=6.4 Hz)(C$_6$'-CH$_3$); 1.27 t (J=7.2 Hz)(OCH$_2$CH$_3$); 3.02(NCH$_3$); 3.43(NCH$_3$); IR(CDCl$_3$) 3555,3437,1707,1658 cm$^{-1}$.

EXAMPLE 3

1,2′,6′-Tri-N-benzyloxycarbonylfortimicin B-4,5-carbamate (3)

A solution of 13.0 g of 4-N-ethoxycarbonyl-1,2′,6′-tri-N-benzyloxycarbonylfortimicin B(2), 5.3 g of sodium bicarbonate and 370 ml of methanol is heated under reflux for 1.5 hours. The methanol is evaporated under reduced pressure and the residue triturated with chloroform. The chloroform suspensions are filtered. Evaporation of the chloroform from the filtrate leaves 12.1 g of product. The latter is chromatographed on 850 g of silica gel using a solvent system prepared from benzene-ethanol [9:1(v/v)] to yield 10.9 g of pure product (3):$[\alpha]_D^{22}$ +2.5° (c 1%,CH$_3$OH); NMR(CDCl$_3$)$\delta$ 0.98d (J=6.0 Hz)(C$_6$'—CH$_3$), 2.83(NCH$_3$), 3.44(OCH$_3$); IR(CDCl$_3$) 3562,3438,3320,1759,1706 cm$^{-1}$.

EXAMPLE 4

2′,6′-Di-N-benzyloxycarbonylfortimicin B-1,2:4,5-bis-carbamate (4)

To a solution prepared from 1.02 g of the compound of Example 3 in 20 ml of dry N,N-dimethylformamide, magnetically stirred, under a nitrogen atmosphere and cooled in an ice bath, is added 0.280 g of 57% oily sodium hydroxide. Stirring is continued for 4 hours with ice bath cooling. Acetic acid (0.8 ml) is then added to the cold suspension. The resulting solution is shaken with a mixture of 100 ml of chloroform and 200 ml of 5% aqueous sodium bicarbonate. The chloroform solution is separated and washed with 200 ml of water. The aqueous solutions are washed in series with three 100-ml portions of chloroform. The chloroform solutions are combined and dried over magnesium sulfate. The chloroform is evaporated under reduced pressure and residual N,N-dimethylformamide is removed by co-distillation with toluene under reduced pressure leaving 1.05 g of a white glass. The latter product (1.01 g) is dissolved in 20 ml of pyridine and 2.0 ml of acetic anhydride is added. The resulting solution is kept at room temperature for 24 hours. The resulting solution is shaken with a mixture of 200 ml of chloroform and 200 ml of 5% aqueous sodium bicarbonate. The chloroform solution is separated and washed with 200 ml of water. The aqueous solution is washed with three 100 ml portions of chloroform. The chloroform solutions are combined and the chloroform is evaporated under reduced pressure. Residual pyridine is removed by co-distillation with toluene under reduced pressure leaving 1.04 g of white glass. The latter (1.01 g) is chromatographed on a column of 100 g of silica gel packed and eluted with a solvent system composed of 1,2-dichloroethane-ethyl acetate [14:16(v/v)]. Initial fractions yield 0.161 g of 1,2′,6′-tri-N-benzyloxcarbonyl-2-O-acetylfortimicin B-4,5-carbamate. Further elution of the column yields 0.594 g of a white glass which is rechromatographed on a column of 40 g of silica gel packed and eluted with a solvent system composed of methylene chloride-ethyl acetate [3:2(v/v)] to yield 0.398 g of product (4):$[\alpha]_D^{21}$ −2.33° (c 1%,CH$_3$OH); NMR(CDCl$_3$) $\delta$ 1.16d(J=7.0 Hz)(C$_6$-CH$_3$); 2.85(NCH$_3$); 3.52(OCH$_3$); IR(CDCl$_3$) 3440,3300, 1750,1697 cm$^{-1}$.

EXAMPLE 5

Fortimicin B-1,2:4,5-bis-carbamate dihydrochloride

Five hundred milligrams of the compound of Example 4 in 30 ml of 0.2 N hydrochloric acid in methanol is hydrogenated under 3 atmospheres of hydrogen for 4 hours in the presence of 0.5 g of 5% palladium on carbon. The catalyst is removed by filtration and the methanol is evaporated under reduced pressure. Residual hydrochloric acid is removed by co-distillation with methanol under reduced pressure leaving 371 mg of product as a white glass$[\alpha]_D^{22}$ +8.8° (c 1%,CH$_3$OH); NMR(D$_2$O)$\delta$ 1.79 (J=7.0 Hz)(C$_6$'—CH$_3$); 3.35(NCH$_3$); 4.03(OCH$_3$), 5.96d(J=3.7 Hz) (C$_1$'-H); IR(KBr) 1737,1722 cm$^{-1}$.

We claim:

1. 2′,6′-Di-N-benzyloxyfortimicin B-1,2:4,5-bis-carbamate.

2. Fortimicin B-1,2:4,5-bis-carbamate or a salt thereof.

* * * * *